(12) United States Patent
DiStefano (10) Patent No.: US 6,908,460 B2
(45) Date of Patent: Jun. 21, 2005

(54) APPARATUS FOR CONVEYING A LIGHT SOURCE TO AN INTRAVENOUS NEEDLE TO KILL BLOOD PATHOGENS

(76) Inventor: Joseph DiStefano, MPD-1 9629 Bay Pines Blvd., St. Petersburg, FL (US) 33708

( * ) Notice: Subject to any disclaimer, the term of this patent is extended or adjusted under 35 U.S.C. 154(b) by 168 days.

(21) Appl. No.: 10/304,891

(22) Filed: Nov. 26, 2002

(65) Prior Publication Data

US 2003/0114842 A1 Jun. 19, 2003

Related U.S. Application Data

(63) Continuation-in-part of application No. 09/940,996, filed on Aug. 28, 2001, now abandoned.

(51) Int. Cl.[7] .............................................. A61B 18/18
(52) U.S. Cl. ............................ 606/7; 606/15; 606/167; 607/88; 607/89; 604/9; 604/20; 604/21; 604/30
(58) Field of Search ............................ 606/2, 3, 7, 10, 606/13–16, 108, 159, 167; 607/88, 89, 92; 604/5.02, 6.08, 6.12, 7–11, 13–22, 27, 30–32, 43, 164.02

(56) References Cited

U.S. PATENT DOCUMENTS

| | | | |
|---|---|---|---|
| 4,608,980 A | * | 9/1986 | Aihara ........................ 606/16 |
| 4,690,140 A | * | 9/1987 | Mecca ......................... 606/159 |
| 4,830,460 A | | 5/1989 | Goldenberg |
| 4,863,432 A | * | 9/1989 | Kvalo ......................... 604/177 |
| 5,053,033 A | | 10/1991 | Clarke |
| 5,123,902 A | * | 6/1992 | Muller et al. ................. 604/21 |
| 5,222,953 A | * | 6/1993 | Dowlatshahi ................ 606/15 |
| 5,292,305 A | | 3/1994 | Boudewijn et al. |
| 5,569,240 A | | 10/1996 | Dowlatshahi |
| 5,891,082 A | | 4/1999 | Leone et al. |
| 6,066,130 A | * | 5/2000 | Gregory et al. ............... 606/15 |
| 6,117,128 A | | 9/2000 | Gregory |
| 6,187,030 B1 | | 2/2001 | Gart et al. |
| 6,197,789 B1 | | 3/2001 | Grainger et al. |

FOREIGN PATENT DOCUMENTS

EP                 000830870 A1 * 3/1998  .......... A61M/25/01

* cited by examiner

*Primary Examiner*—A. Farah
(74) *Attorney, Agent, or Firm*—Larson & Larson, PA; Herbert W. Larson (57) ABSTRACT

A tip of a needle is inserted into large vein of a patient. The needle is mounted in a butterfly device axially engaged to a generally cylindrical housing containing a Y-connector. A pharmaceutically acceptable solution is fed to the needle through the Y-connector to the housing. A quartz optic fiber is fed through the housing and needle to the tip of the needle in the patient's venous system. A source of UV and visible light directs both UV and visible light alternatively through the optic fiber to the patient's venous system to kill pathogens in the venous system.

20 Claims, 7 Drawing Sheets

APPARATUS FOR CONVEYING A LIGHT SOURCE TO AN INTRAVENOUS NEEDLE TO KILL BLOOD PATHOGENS

PRIOR APPLICATION

This application is a continuation in part from application Ser. No. 09/940,996, filed Aug. 28, 2001 now abandoned.

FIELD OF THE INVENTION

This invention relates to an apparatus emitting light rays to kill pathogenic organisms. More particularly, it refers to an apparatus for the conveying of alternating UV and visible light through a quartz fiber optic cable to a needle inserted into a patient's venous blood.

BACKGROUND OF THE INVENTION

It is well known to use UV light to kill pathogens in water. Many systems exist to expose water to UV light with the object of destroying pathogens in the water. It also is well known to guide fiber optic instruments into arterial blood vessels. See U.S. Pat. No. 4,830,460 where the ultraviolet laser energy is used for the ablation of atherosclerotic plaque; U.S. Pat. No. 5,053,033 where an optical fiber delivers UV radiation to a blood vessel site following angioplasty to kill aortic smooth muscle cells at the site; U.S. Pat. No. 5,891,082 where a catheter body has a light-emitting section at a distal end for curing a stent delivered to a blood vessel site; U.S. Pat. No. 6,117,128 where laser energy coupled to an optical fiber and transported by a catheter to treat vascular thrombosis disorders in the brain; and U.S. Pat. No. 6,187,030 where a flexible fiber optic bundle connected to a light source is used for treatments of internal and external diseases.

In spite of the wide use of UV light by the medical profession no apparatus has been developed for cleansing blood of pathogens such as fungi, virus, bacteria and molds. Such an apparatus is in critical need.

SUMMARY OF THE INVENTION

This invention is the discovery of an apparatus for destroying pathogens in the venous blood of a patient. A rear portion of a needle is mounted in a butterfly housing with a tip extending outwardly. The tip of the needle in the apparatus is inserted into a large vein of a patient. A pharmaceutically acceptable solution stream flows through the needle arm of a Y-housing and through the needle to its tip. A first portion of a quartz optic fiber passes through another arm of the Y-housing and through the needle to a tip. A second end of the quartz optic fiber is connected to a first end of a fiber optic bundle which is connected at a second end to a source of both UV and visible light. The apparatus is used to expose venous blood to about thirty minutes of UV light wavelength of 200–450 nanometers and then for about thirty minutes to visible light.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION OF THE INVENTION

Throughout the following detailed description the same reference numerals refer to the same elements in all figures.

Figure 1:
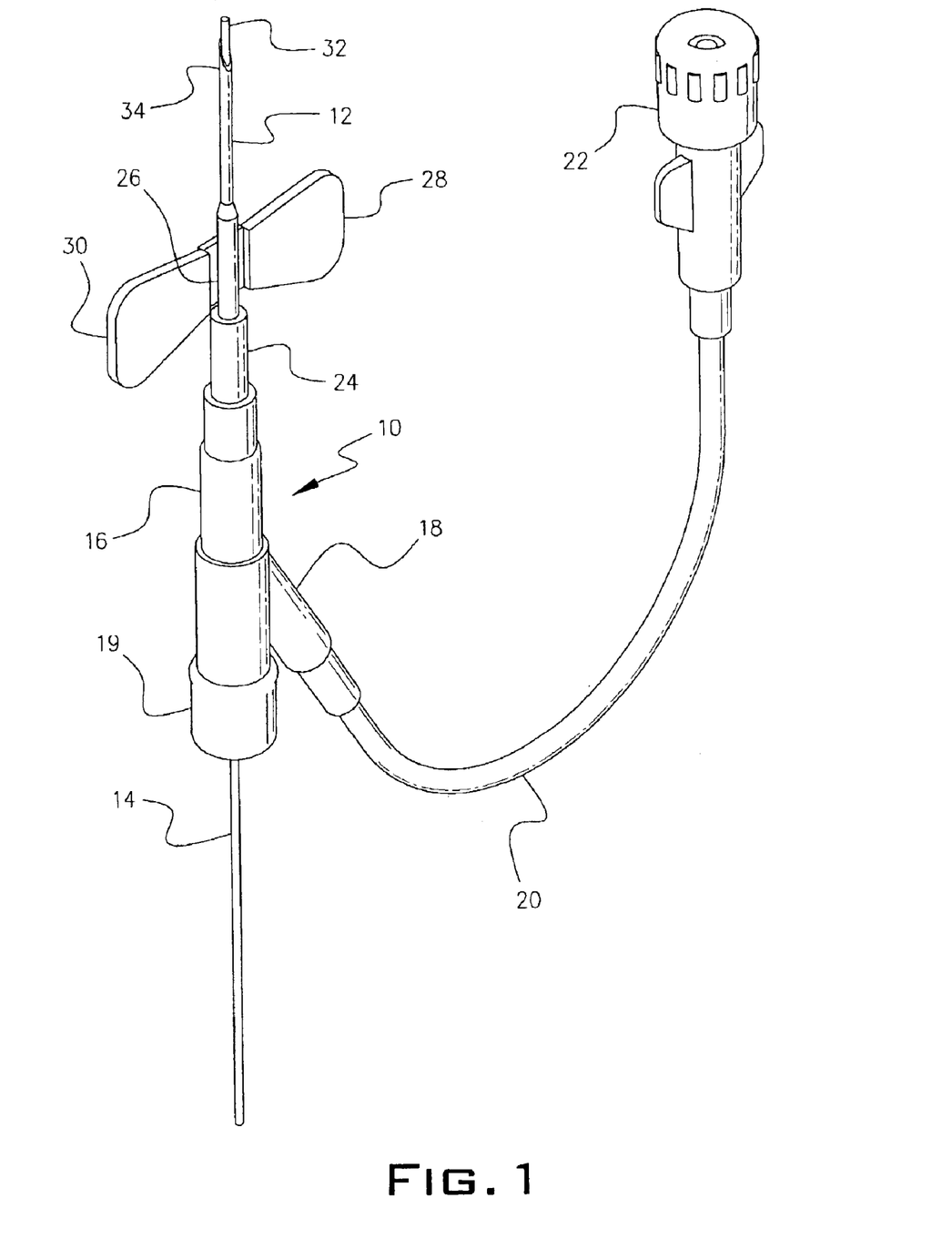
FIG. 1 is perspective view of a needle, an optic fiber and a saline water source housed in a butterfly throw away device.

Referring first to FIG. 1, the housing 10 is a plastic disposable device in a Y-configuration having a first arm 18 and a second arm 19 leading to a cylindrical body 16. A quartz optic fiber 14 is threaded through the arm 19 of the housing 10. Arm 18 is connected to a pharmaceutically acceptable solution delivery conduit 20 from a connector 22. The cylindrical body 10 has a cylindrical end portion 24 receiving a hub 26 integral with butterfly wings 28 and 30. The hub 26 retains an upper portion of needle 12 in place. The optic fiber 14 is threaded from arm 19, through body 16 and through the needle 12 positioned in hub 26. An end 32 of the optic fiber 14 is visible at the tip 34 of needle 12.

Figure 2:
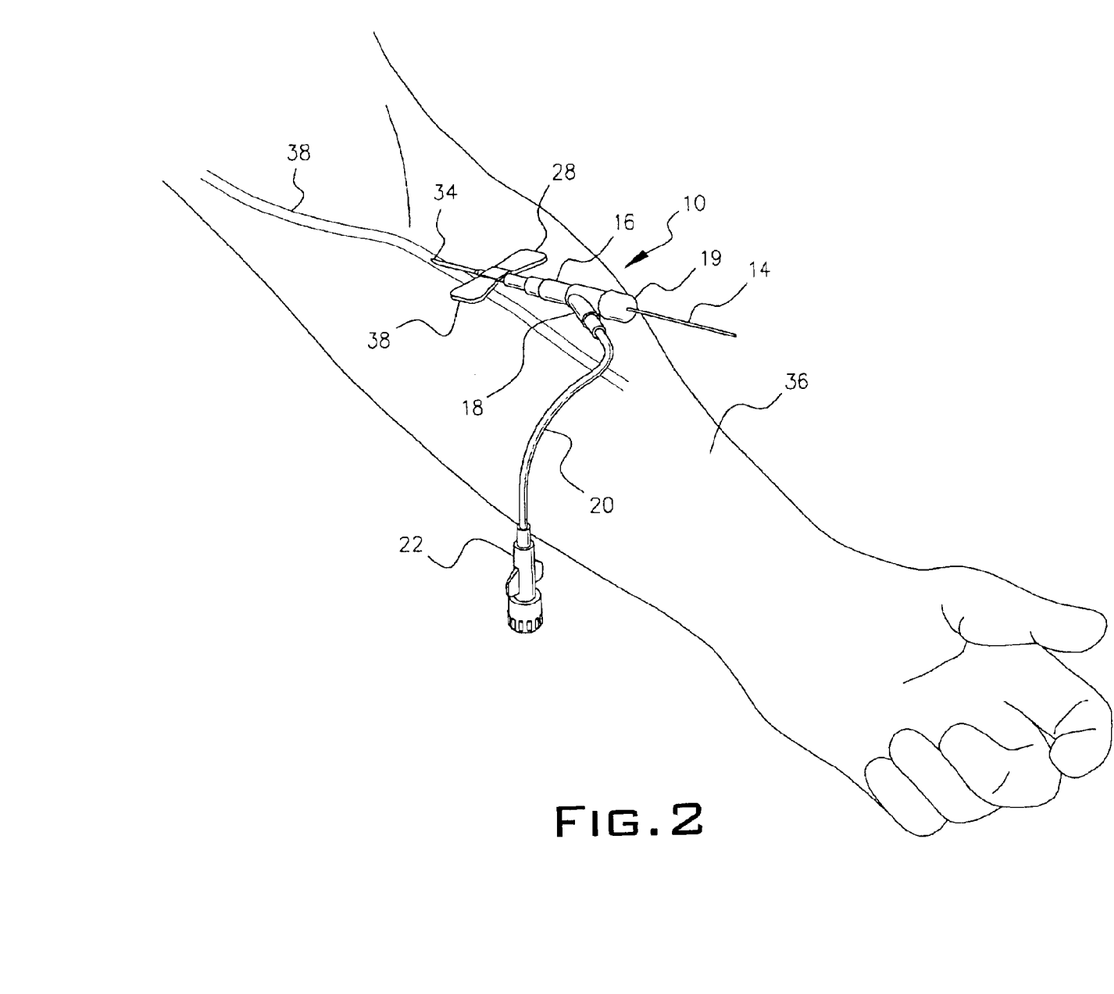
FIG. 2 is a perspective view of the device of FIG. 1 prior to inserting the needle in a vein of a patient.
Figure 3:
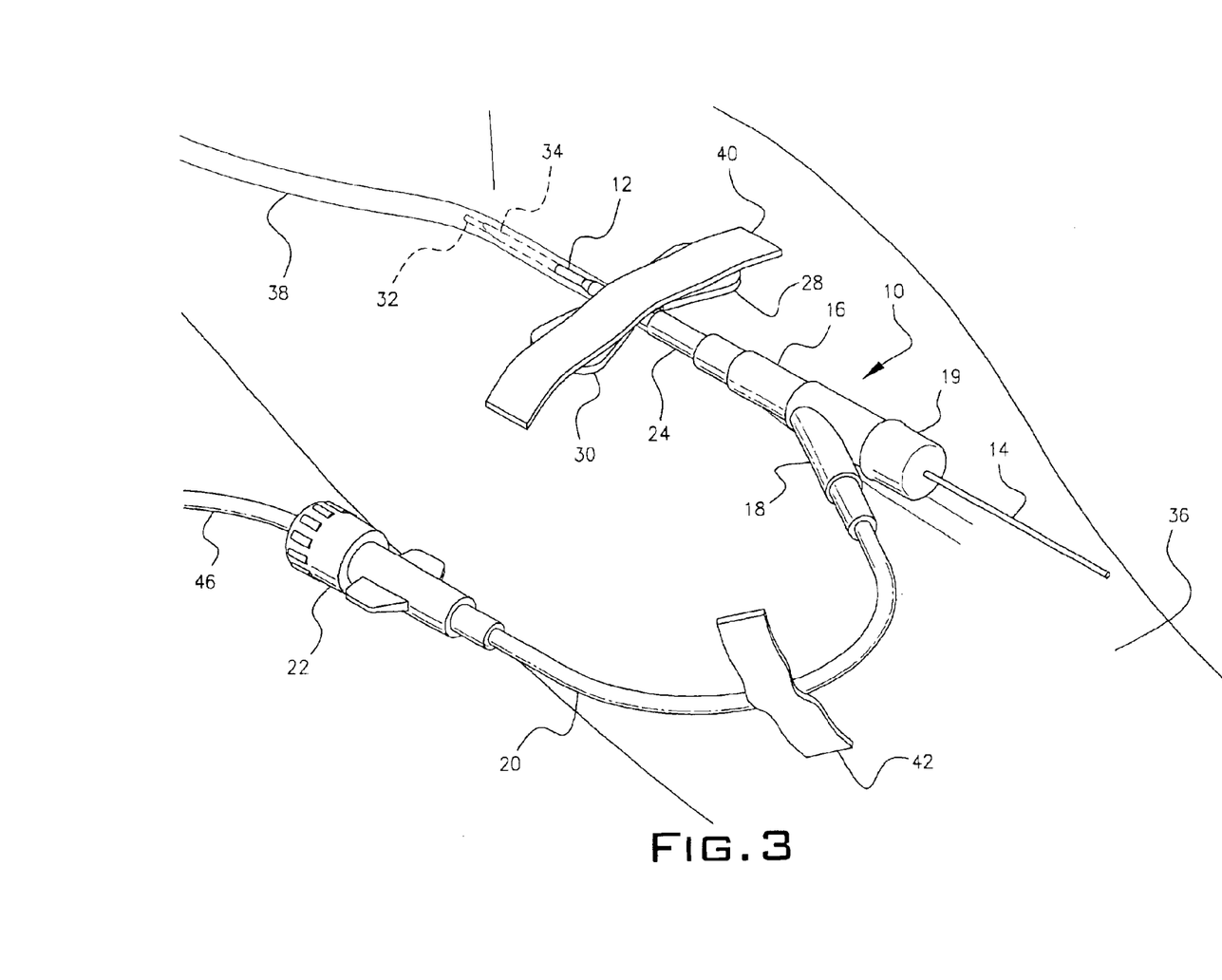
FIG. 3 is a perspective view of the device taped to a patient's arm with the needle inserted into the patient's vein.

In FIG. 2 the arm 36 of a patient is shown with a vein 38 about to be penetrated by the point 34 of needle 12. After the needle 12 is inserted into vein 38 as shown in FIG. 3 the butterfly wings 28 and 30 are taped 40 to arm 36. In like manner the pharmaceutically acceptable solution delivery conduit 20 is taped 42 to the patients arm 36.

Figure 4:
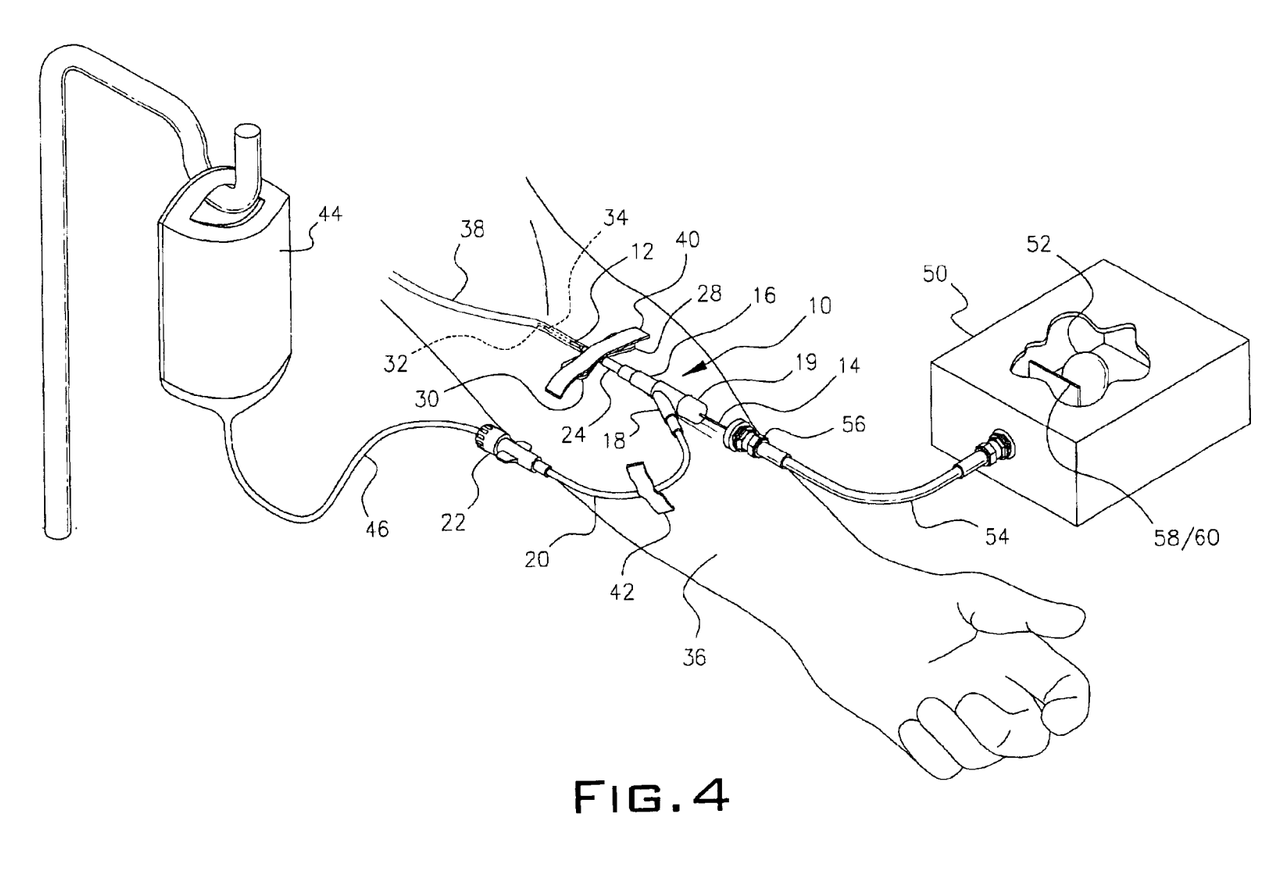
FIG. 4 is a schematic view of the apparatus of this invention.
Figure 5:
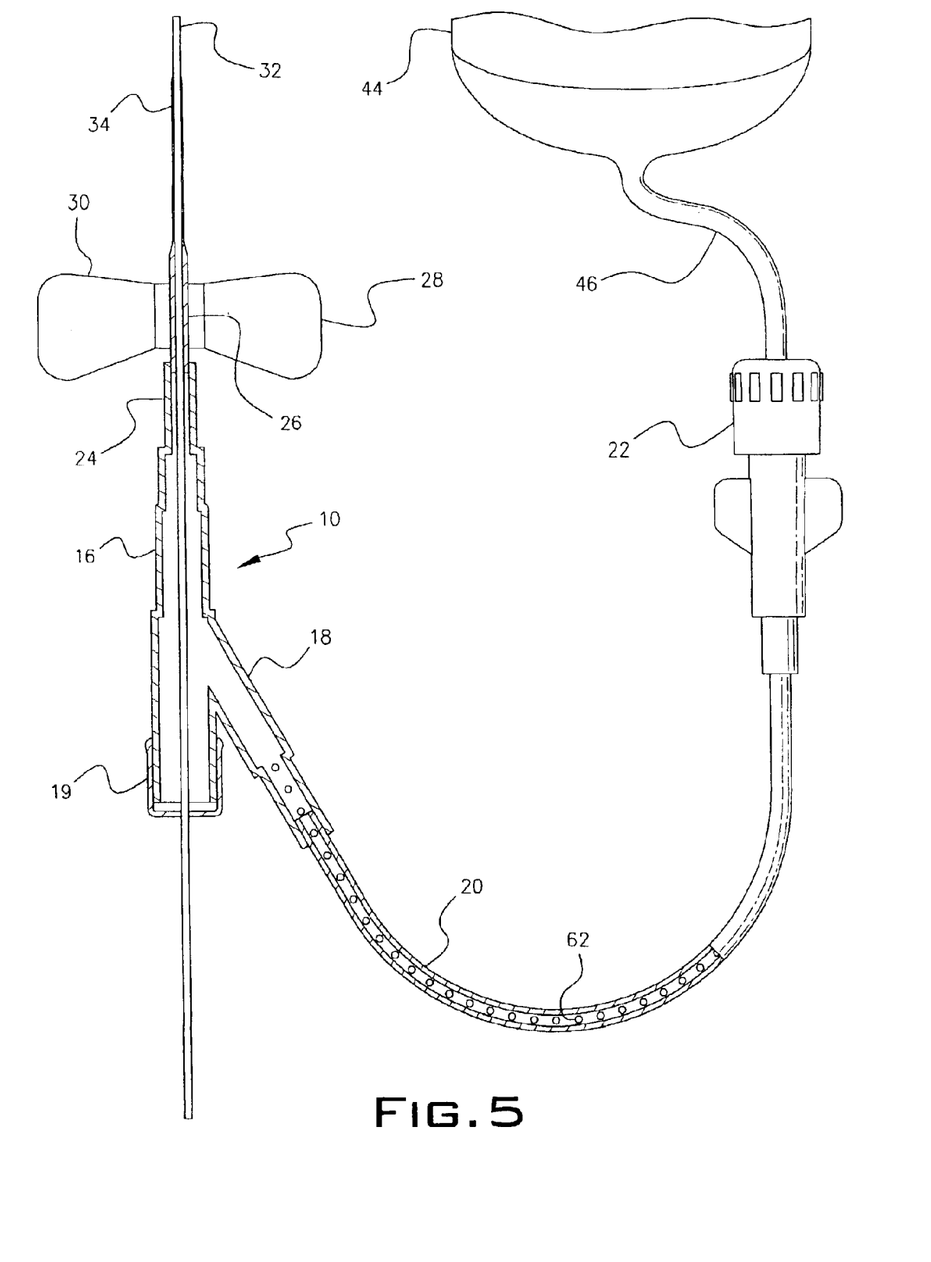
FIG. 5 is an open conduit view of the saline drip from the solution source.

As seen in FIGS. 4 and 5, a solution bag 44 containing normal saline, glucose or other pharmaceutically acceptable solution has a conduit 46 leading to a connector 22 which determines the drip rate 62 to needle 12. A continuous rate of one drop per second is sufficient to keep tip 34 and end 32 of the optic fiber 14 clear of blocking blood cells. The UV or visible light source emanates from a box 50 containing a bulb 52 which can have rotating filter, 58 and 60 around the bulb 52 to permit either UV or visible light to travel through a bundle of quartz optic fibers 54 to a connector 56 engaging to optic fiber 14. The bundle of optic fibers 54 is defined for purposes of this application as one or more optic fibers. If only one optic fiber constitutes the bundle, then it must exceed the diameter of the quartz optic fiber 14.

Figure 6:
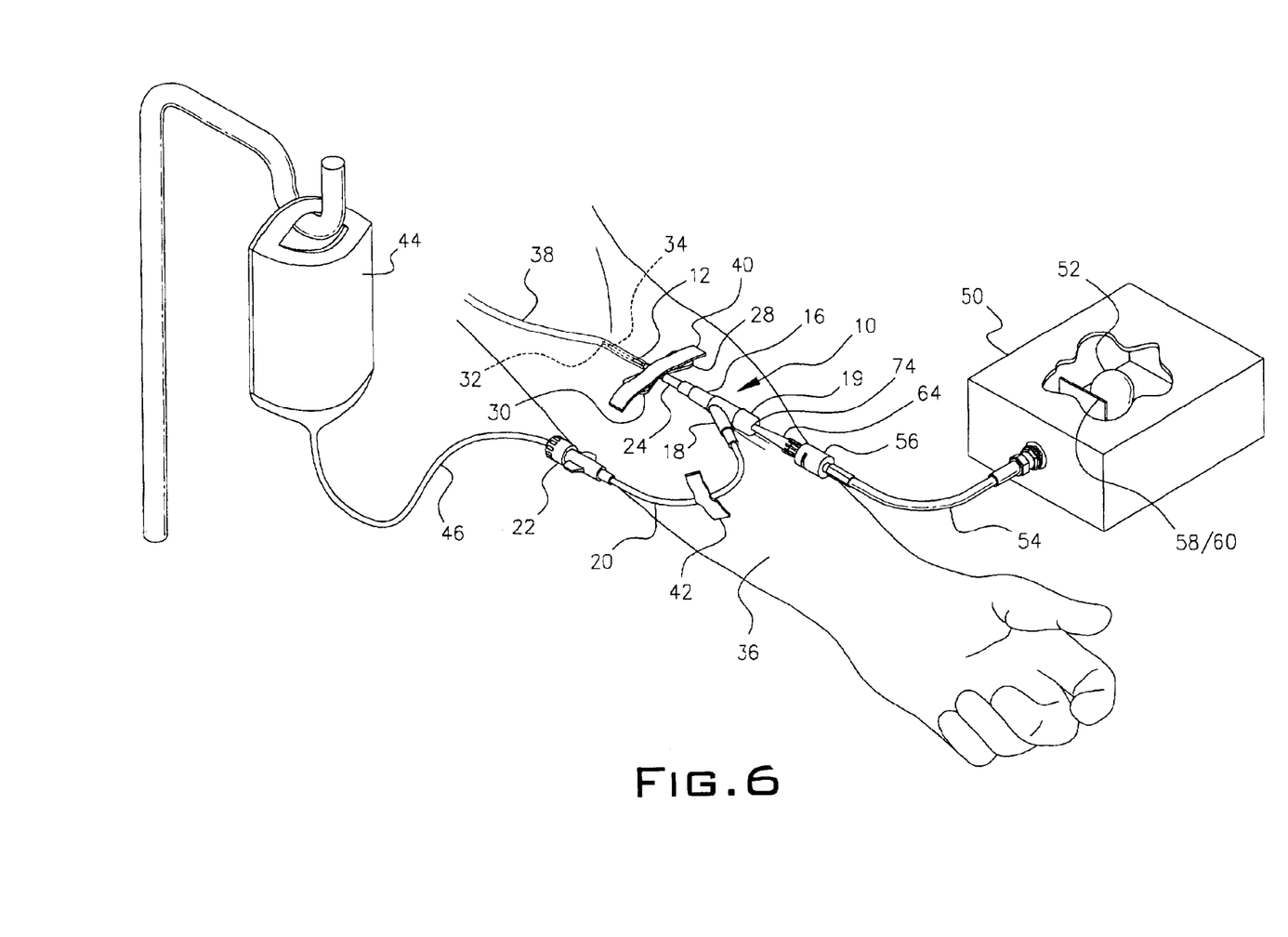
FIG. 6 is a schematic view of the apparatus of this invention employing an alternative quartz optic fiber centering connector.
Figure 7:
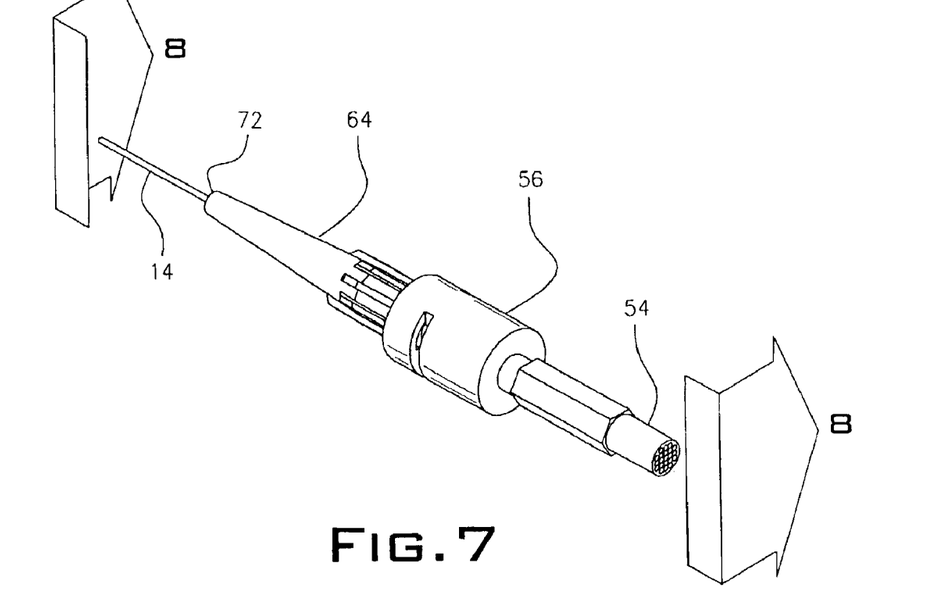
FIG. 7 is a blow-up of the alternative quartz optic fiber tapered connector attached to a bundle of optic fibers.
Figure 8:
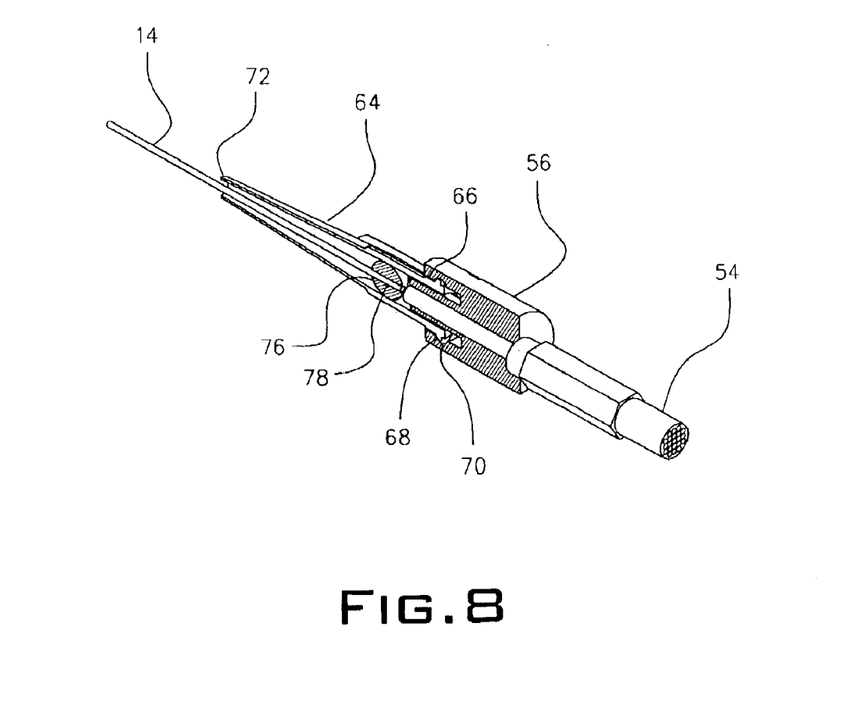
FIG. 8 is a longitudinal sectional view of the alternative quartz optic fiber tapered connector engaged to the bundle of optic fibers.

An alternate hollow tapered connector 64 as shown in FIGS. 6–8 can join the bundle of quartz optic fibers 54 and its connector 56 to the second arm 19 of housing 10. Tapered connector 64 has a wide mouth 66 with external threads 68 that threadably engage internal threads 70 on connector 56. The narrow pointed end 72 of tapered connector 64 is inserted into a top end 74 of second arm 19. A ball 76 movably mounted within tapered connector 64 has a central bore 78 through which optic fiber 14 is passed. When threads 70 of connector 56 are threaded to threads 68 in tapered connector 64, the ball is forced downwardly in tapered connector 64 and the optic fiber 14 is perfectly centered to insure that UV light passes directly to the needle tip 34.

The needle 12 is usually about 19 gauge for an adult and about 25 for a pediatric patient. The diameter of the quartz optic fiber 14 will be determined by the size of the needle.

The treatment usually lasts one hour with the first thirty minutes under UV light of 200–450 nanometer wavelength and then for thirty minutes at visible light of 450 to 1100 nanometer wavelength.

The butterfly wings 28 and 30 together with its hub is made from a typical medically acceptable plastic. The housing 10 and the conduits 20 and 46 also are made from a medically acceptable plastic.

Pathogens in the venous blood supply killed by the use of the apparatus include bacteria, virus, fungi, molds and other unclassified pathogens.

The above description has described the specific apparatus of this invention. However, it will be within the skill of one having ordinary skill in the medical field to make modifications without departing from the spirit and scope of the underlying inventive concept of this apparatus.

Having described the invention in detail the following is claimed:

1. An apparatus for destroying pathogens in a venous blood vessel comprising:
   (a) a housing having a first and second passageway leading to a cylindrical body, an end portion of the body distal from the first and second passageway enclosing an annular needle housing;
   (b) a needle having a first portion mounted in the annular needle housing and a second portion extending outwardly to a tip for inserting into a vein of a patient;
   (c) a sealed enclosure containing a pharmaceutically acceptable solution having a conduit leading to one of the passageways;
   (d) a first end portion of a quartz optic fiber passing through one of the passageways and through the needle to the tip;
   (e) a second portion of the quartz optic fiber connected through a hollow tapered connector to a first end of a fiber optic bundle, the fiber optic bundle connected at a second end to a source of UV and visible light whereby the UV and visible light are alternatively conducted to the tip of the needle, while the solution is flowing through the needle to the tip; and
   (f) the second portion of the quartz optic fiber centered through a center bore in a ball positioned in the hollow tapered connector, the tapered connector attached to a terminal for the quartz fiber optic bundle.

2. An apparatus according to claim 1 wherein the annular needle housing has a butterfly wing configuration attached to an exterior surface of the housing.

3. An apparatus according to claim 1 wherein the needle is about a 19 gauge.

4. An apparatus according to claim 1 wherein the conduit from the solution in a bag passes through a connector monitoring the flow of solution.

5. The apparatus according to claim 4 wherein the connector is adapted to permit a flow of about one drop per second.

6. The apparatus according to claim 1 wherein the source of UV and visible light is a lighted bulb separated from the second end of the fiber optic bundle by either a UV or visible light filter.

7. The apparatus according to claim 1 wherein the hollow tapered connector connecting the second portion of the quartz optic fiber to the first end of the fiber optic bundle contains the ball movable within a portion of the tapered connector, the ball having a central bore for centering the second portion of the quartz optic fiber with respect to the fiber optic bundle.

8. An apparatus for destroying pathogens in a venous blood vessel comprising:
   (a) a housing having a first and second arm leading to a cylindrical body, an end portion of the cylindrical body distal from the first and second arms enclosing a needle housing;
   (b) a needle having a first portion mounted in the needle housing and a second portion extending outwardly to a tip adapted to be inserted into a vein of a patient;
   (c) a liquid solution source having a conduit leading to the first arm;
   (d) a first end portion of a quartz optic fiber passing through the second arm and through the needle to the tip;
   (e) a second portion of the quartz optic fiber centered through a center bore in a ball movably positioned in a hollow tapered connector, the hollow tapered connector attached at a wide mouth to a terminal for a quartz fiber optic bundle and at a narrow pointed end to the second arm of the housing; and
   (f) the fiber optic bundle connected at an end distal from the terminal to a source of UV and visible light whereby the UV and visible light is conducted to the tip of the needle while the solution is flowing through the needle to the tip.

9. The apparatus according to claim 8 wherein the liquid solution source is a bag containing normal saline.

10. The apparatus according to claim 8 wherein the source of UV and visible light is a lighted bulb spaced apart, from an end of the fiber optic bundle distal from the connection with the tapered connector, by either a UV or visible light filter.

11. The apparatus according to claim 8 wherein the first portion of the needle is mounted in a hub.

12. The apparatus according to claim 8 wherein the tapered connector has external threads at the wide mouth threaded to internal threads in the terminal for the quartz fiber optic bundle.

13. The apparatus according to claim 8 wherein the pointed end of the tapered connector is engaged in a top end of the second arm.

14. A method of treating venous blood of a patient by exposing the venous blood to a UV and a visible light comprising:
   (a) providing a Y-shaped housing having an annular internal diameter wherein a terminal end of the Y-shaped housing encloses the hub of a needle housing;
   (b) providing a needle having a first end mounted in the hub and a second end tip protruding outside the hub;
   (c) providing a saline solution bag with a conduit from the bag directed to a first arm of the Y-shaped housing;
   (d) providing a quartz optic fiber and passing a first end of the quartz optic fiber through a second arm of the Y-shaped housing and through the needle to the tip, connecting a second end of the quartz optic fiber to a first end of a quartz fiber optic bundle which is connected at a second end separately to the UV and the visible light source wherein the second end of the quartz fiber optic is centered through a center bore in a ball positioned in a hollow tapered connector, the tapered connector attached to a terminal for the quartz fiber optic bundle;
   (e) providing the UV light at 200 to 400 nanometers and the visible light at 450 to 1100 nanometers;
   (f) inserting said needle into a vein of a patient in which a blood stream is flowing whereby the UV and visible light and saline solution are conducted to the tip of the needle; and killing pathogens in the venous blood by exposure to the UV and visible light.

15. The method of claim 14 wherein the terminal end of the Y-shaped housing is provided with an exterior annular diameter decreasing in width from the first and second arm.

16. The method of claim 14 wherein the needle housing is provided with a butterfly wing configuration attached to an exterior surface of the hub.

17. The method of claim 14 wherein the needle is provided at about 19 gauge.

18. The method of claim 14 wherein the conduit from the saline solution bag is passed through a connector monitoring the flow of solution.

19. The method of claim 14 wherein the visible light source is provided by a light bulb separated from the second end of the quartz fiber optic bundle by either a UV or visible light filter.

20. The method of claim 18 wherein the connector is further provided as a structure permitting a flow of about one drop per second.

* * * * *